US012661531B1

(12) United States Patent
Kang

(10) Patent No.: US 12,661,531 B1
(45) Date of Patent: Jun. 23, 2026

(54) CARTRIDGE DETACHABLE NON-FOCUSED HANDPIECE AND NON-FOCUSED ULTRASOUND MEDICAL DEVICE INCLUDING THE SAME

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 0 days.

(21) Appl. No.: 19/270,992

(22) Filed: Jul. 16, 2025

(30) Foreign Application Priority Data

Jan. 14, 2025 (KR) ........................ 10-2025-0005422

(51) Int. Cl.
*A61N 7/00* (2006.01)
(52) U.S. Cl.
CPC ........ *A61N 7/00* (2013.01); *A61N 2007/0034* (2013.01); *A61N 2007/0078* (2013.01)
(58) Field of Classification Search
CPC .............. A61N 7/00; A61N 2007/0034; A61N 2007/0078
See application file for complete search history.

(56) References Cited

U.S. PATENT DOCUMENTS

| | | | | | |
|---|---|---|---|---|---|
| 2015/0335467 | A1* | 11/2015 | Varga | ........................ | A61F 7/02 |
| | | | | | 607/104 |
| 2022/0008112 | A1* | 1/2022 | Sverdlik | .................. | A61N 7/00 |
| 2024/0189630 | A1* | 6/2024 | Kang | ........................ | A61N 7/00 |

FOREIGN PATENT DOCUMENTS

| | | | |
|---|---|---|---|
| KR | 10-2016-0145752 | A | 12/2016 |
| KR | 10-2019-0080765 | A | 7/2019 |
| KR | 10-2022-0002932 | A | 1/2022 |
| KR | 10-2023-0054085 | A | 4/2023 |
| KR | 10-2551710 | B1 | 6/2023 |
| KR | 10-2809698 | B1 | 5/2025 |

OTHER PUBLICATIONS

Korean Office Action on Mar. 8, 2025 in corresponding Korean Patent Application No. 10-2025-0005422 (3 pages in English, 4 pages in Korean).
Korean Office Action on Apr. 17, 2025 in corresponding Korean Patent Application No. 10-2025-0005422 (3 pages in English, 4 pages in Korean).

* cited by examiner

*Primary Examiner* — Pascal M Bui Pho
*Assistant Examiner* — Gabriel Victor Popescu
(74) *Attorney, Agent, or Firm* — NSIP Law

(57) ABSTRACT

A cartridge detachable non-focused handpiece comprises a handpiece-shaped housing and a cartridge that is detachably attached to the housing. The housing includes a coupling groove into which a part of the cartridge is inserted, an output switch configured to manipulate an ultrasound wave output, attachment/detachment buttons configured to control attachment and detachment of side surface of the cartridge, and a power supply part configured to supply a power to the cartridge. The cartridge includes a contact part having an ultrasound generation module and being configured to contact a skin of a subject, an insertion part being protruded in a shape corresponding to an inner shape of the coupling groove and having an attachment/detachment part which is engageable by pressing the detachment buttons and a substrate electrically connected to the power supply part to drive the ultrasound generation module.

6 Claims, 6 Drawing Sheets

1

1

1

100

200

200

211

260

CARTRIDGE DETACHABLE NON-FOCUSED HANDPIECE AND NON-FOCUSED ULTRASOUND MEDICAL DEVICE INCLUDING THE SAME

CROSS-REFERENCE TO RELATED APPLICATIONS

This application claims priority to Korean Patent Application No. 10-2025-0005422 filed on Jan. 14, 2025, the entire contents of which are incorporated herein by reference.

TECHNICAL FIELD

The present disclosure relates to a cartridge detachable non-focused handpiece and a non-focused ultrasound medical device including the same; and, more specifically, to a cartridge detachable non-focused handpiece and a non-focused ultrasound medical device including the same, in which usability and product life are improved because cartridges capable of performing various types of non-focused ultrasound treatment with a single handpiece and medical device can be selectively coupled by replacing a cartridge that is coupled with a handpiece and performs treatment as required, and only a cartridge with a short service life can be easily replaced and reused.

BACKGROUND

Ultrasound treatment includes high-intensity focused ultrasound (HIFU) that focuses and radiates high-intensity ultrasound waves with a high intensity over 1,000 W/cm², low-intensity focused ultrasound (LIFU) that focuses and radiates ultrasound waves stronger than those of heat treatment but weaker than those of HIFU, and low-intensity pulsed ultrasound (LIPUS) that radiates non-focused ultrasound waves weaker than those of HIFU.

The treatment using non-focused ultrasound waves is used for skin lifting to cause necrosis by heating subcutaneous tissue, or is used for reducing joint stiffness and muscle spasms and for fracture healing and cartilage cell regeneration in sports medicine and musculoskeletal treatment. Compared to the treatment using laser, IPL, RF, fractional laser, LED, or the like, the treatment using non-focused ultrasound waves is advantageous in less trauma and pain and excellent skin regeneration effects.

Recently, as interest in appearance and skin care increases, the interest in treatment using non-focused ultrasound waves is increasing. Further, it is required to provide customized non-focused ultrasound waves according to treatment areas with different skin thicknesses, such as skin around eyes, skin under chin, and the like on the face, to perform effective non-focused ultrasound treatment.

In order to output the customized non-focused ultrasound waves to the treatment portion or the treatment area, it is required to perform the treatment by replacing the handpiece. However, it requires time and effort to connect the ultrasound beauty medical device main body and the handpiece, and malfunction or failure may occur when they are connected incorrectly. In addition, even in the case where a plurality of handpieces are prepared according to the treatment portions, if the transducer in the handpiece breaks down due to long-term use or only the cartridge of the handpiece needs to be replaced due to other reasons, the entire handpiece needs to replaced, so that the cost of purchasing a new handpiece arises.

(Patent Document 1) Korean Laid-open Patent Publication No. 10-2022-0002932 "Ultrasound transducer and system for skin treatment"

SUMMARY

The present disclosure has been made to solve the above-described problems, and an object of the present disclosure is to provide a cartridge detachable non-focused handpiece and a non-focused ultrasound medical device including the same, in which usability and product life are improved because cartridges capable of performing various types of non-focused ultrasound treatment with a single handpiece and medical device can be selectively coupled by replacing a cartridge that is coupled with a handpiece and performs treatment as required, and only a cartridge with a short service life can be easily replaced and reused.

In addition, an object of the present disclosure is to provide a cartridge detachable non-focused handpiece and a non-focused ultrasound medical device including the same, which can improve the treatment efficiency by generating non-focused ultrasound waves only when it is in contact with the skin, and can prevent unnecessary ultrasound wave generation and unnecessary treatment due to unintended non-focused ultrasound waves because the non-focused ultrasound waves are generated only when it is in contact with the skin and can allow the treatment to be performed.

In addition, an object of the present disclosure is to provide a cartridge detachable non-focused handpiece and a non-focused ultrasound medical device including the same, which can prevent unnecessary coolant circulation by linking whether or not the coolant circulates in the cartridge with whether or not the cartridge is attached, prevent coolant leakage or undercirculation during the cartridge attachment/detachment process, and reduce skin pain and swelling during the treatment by the cooling function.

The drawbacks to be solved by the present disclosure are not limited to the above-described drawbacks, and other drawbacks that are not mentioned can be clearly understood by those skilled in the art from the description below.

In order to solve the above-described drawbacks, the present disclosure is characterized in that it provides a cartridge detachable non-focused handpiece comprising a handpiece-shaped housing and a cartridge that is detachably attached to the housing.

The housing includes a coupling groove formed on one surface thereof into which a part of the cartridge is inserted and attached, an output switch formed on an upper surface thereof and configured to manipulate an ultrasound wave output, attachment/detachment buttons formed on both side surfaces thereof and configured to control attachment and detachment of side surface of the cartridge; and a power supply part configured to supply a power to the cartridge. The cartridge includes a contact part formed at one end thereof, the contact part having an ultrasound generation module embedded therein and being configured to contact a skin of a subject, an insertion part formed at the other end thereof, the insertion part being protruded in a shape corresponding to an inner shape of the coupling groove and having an attachment/detachment part which is formed at side surfaces of the insertion part to be inserted into the coupling groove and is engageable by pressing the detachment buttons, and a substrate electrically connected to the power supply part to drive the ultrasound generation module. In the cartridge, the insertion part is inserted into and fixedly attached to the coupling groove, and the ultrasound generation module is configured to generate non-focused ultrasound waves using the power supply part.

In addition, the insertion part has a pressure sensor embedded in a contact surface to be in contact with the power supply part, and the pressure sensor is configured to detect whether or not the cartridge and the housing are coupled, and the ultrasound generation module is configured to be driven only when the coupling of the cartridge and the housing is detected.

In addition, a coupling protrusion protrudes from an outer surface of the insertion part, a coupling rail to be engaged with the coupling protrusion is formed on an inner surface of the coupling groove, and the coupling protrusion slides along the coupling rail when the insertion part is inserted into the coupling groove.

In addition, the ultrasound generation module includes a transducer configured to generate ultrasound waves, and a cooling block configured to absorb heat from the transducer. A water block to be in contact with an upper surface of the cooling block and through which cooling water moves, and a pair of nipples formed on an upper surface of the water block and through which cooling water is introduced and discharged are formed at the cartridge. Cooling water supply holes into which the nipples are inserted to provide cooling water to the water block are formed at the housing. When the cartridge is coupled with the housing, the cooling water provided from the cooling water supply holes circulates through the water block and absorbs heat from the transducer.

The cooling water supply holes have therein check valves so that the nipples are sealed when the nipples are separated from the cooling water supply holes, and the cooling water supply holes are opened when the nipples are inserted into the cooling water supply holes to provide and discharge the cooling water from the handpiece.

In addition, the cartridge further includes a skin cooling part configured to cool the skin of the subject, wherein the skin cooling part includes a cooling surface formed along an edge of the contact part to cool the skin of the subject, and a thermoelectric element configured to absorb heat from the cooling surface, wherein the cooling surface forms a cooling wall configured to cool the skin layer of the subject around the ultrasound waves transmitted from the ultrasound generation module to the skin of the subject.

In addition, the cartridge further includes a skin stimulation part configured to stimulate the skin of the subject, wherein the skin stimulation part includes an EMS pad that is provided at the contact part and provide electrical stimulation to a treatment portion of the subject, and an EMS control module configured to drive and control the EMS pad, and wherein an EMS driving switch configured to control driving of the EMS control module is formed on an outer surface of the housing.

In order to solve the above-described drawbacks, the present disclosure is characterized in that it provides a non-focused ultrasound medical device including the above-described cartridge detachable non-focused handpiece.

In this manner, the present disclosure has an effect of improving usability and product life because cartridges capable of performing various types of non-focused ultrasound treatment with a single handpiece and medical device can be selectively coupled by replacing a cartridge that is coupled with a handpiece and performs treatment as required, and only a cartridge with a short service life can be easily replaced and reused.

In addition, the present disclosure has an effect of improving the treatment efficiency by generating non-focused ultrasound waves only when it is in contact with the skin, and preventing unnecessary ultrasound wave generation and unnecessary treatment due to unintended non-focused ultrasound waves because the non-focused ultrasound waves are generated only when it is in contact with the skin and can allow the treatment to be performed.

In addition, the present disclosure has an effect of preventing unnecessary coolant circulation by linking whether or not the coolant circulates in the cartridge with whether or not the cartridge is attached, preventing coolant leakage or undercirculation during the cartridge attachment/detachment process, and reducing skin pain and swelling during the treatment by the cooling function.

The drawbacks to be solved by the present disclosure are not limited to the above-described drawbacks, and other drawbacks that are not mentioned can be clearly understood by those skilled in the art from the description below.

DETAILED DESCRIPTION

Figure 1:
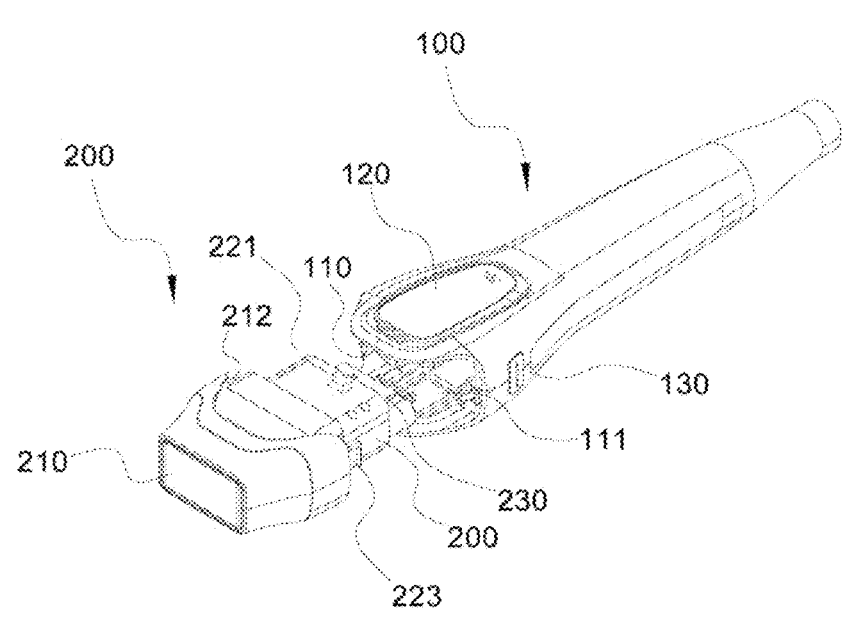
FIG. 1 is a perspective view showing an example of a cartridge detachable non-focused handpiece according to the present disclosure.
Figure 2:
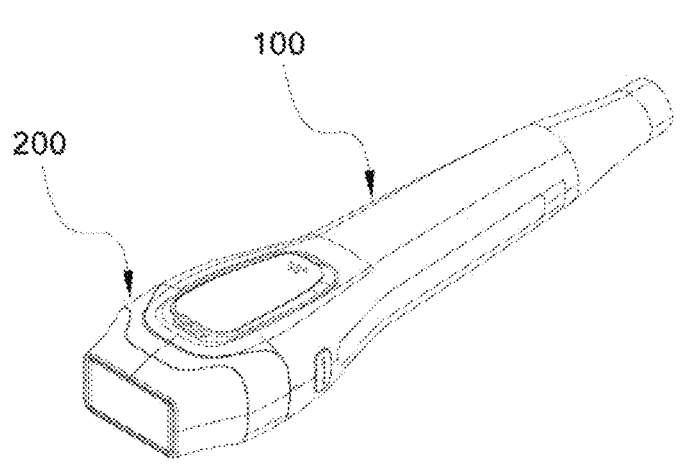
FIG. 2 is a perspective view showing an example of coupling of a cartridge detachable non-focused handpiece according to the present disclosure.
Figure 3:
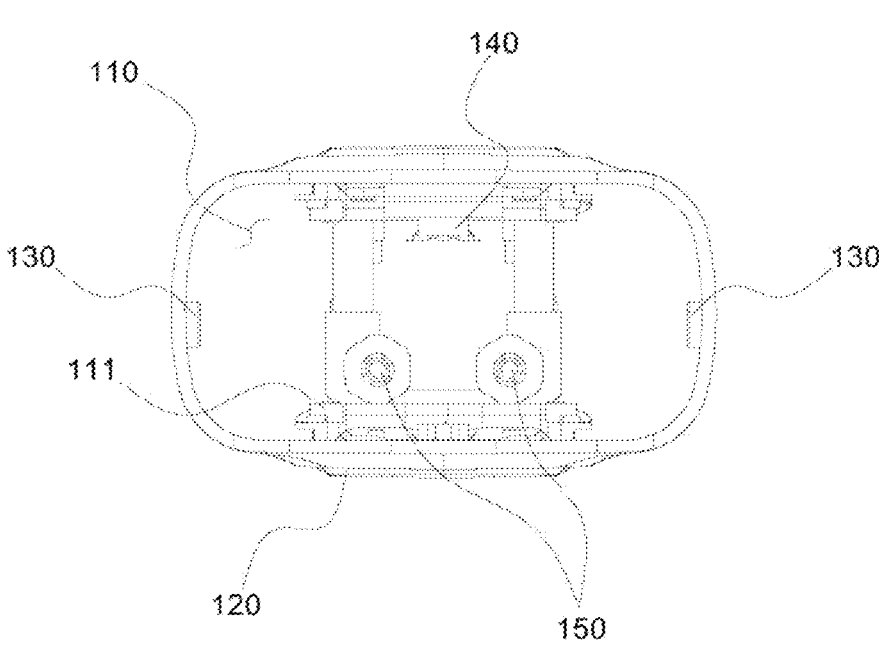
FIG. 3 is a bottom view showing a housing according to the present disclosure.

The present disclosure can be variously modified and may have various embodiments, and specific embodiments will be illustrated in the drawings and described in detail.

However, this is not intended to limit the present disclosure to specific embodiments, and it should be understood that all modifications, equivalents, and alternatives included in the spirit and technical scope of the present disclosure are included. Like reference numerals have been used for like parts in describing each drawing.

When a certain component is said to be "connected" or "coupled" to another component, it can be directly connected or coupled to another component, but it should be understood that other components can also exist therebetween. On the other hand, when a certain component is said to be "directly connected" or "directly coupled" to another component, it should be understood that no other elements exist therebetween.

The terms used in the present specification are used only to describe a specific exemplary embodiment, and are not intended to limit the present disclosure. The singular expression includes the plural expression unless the context clearly described otherwise. In the present specification, it should be understood that terms such as "comprise" or "have" specifies the presence of the embodied feature, number, step, operation, component, part, or a combination thereof, but does not exclude the presence or addition possibility of one or more other features, numbers, steps, operations, components, parts, or combinations thereof in advance.

Hereinafter, embodiments of the present disclosure will be described with reference to the accompanying drawings. Like reference numerals in each drawing refer to like parts. In describing the present disclosure, if it is determined that detailed description of related known technologies or configurations may unnecessarily obscure the gist of the present disclosure, the detailed description thereof will be omitted.

The present disclosure relates to a cartridge detachable non-focused handpiece and a non-focused ultrasound medical device including the same, in which usability and product life are improved because cartridges capable of performing various types of non-focused ultrasound treatment with a single handpiece and medical device can be selectively coupled by replacing a cartridge that is coupled with a handpiece and performs treatment as required, and only a cartridge with a short service life can be easily replaced and reused. A cartridge detachable non-focused handpiece 1 includes a handpiece-shaped housing 100 and a cartridge 200 that can be detachably attached to the housing 100.

The housing 100 is formed in the shape of the handpiece 1, and a coupling groove 110 to be coupled with the cartridge 200 is recessed at one end of the housing 100 where one surface is opened.

The coupling groove 110 is recessed in a shape corresponding to that of an insertion part 220 of the cartridge 200, and the cartridge 200 is fixed to the housing 100 when the insertion part 220 slides toward the coupling groove 110 and is completely inserted thereinto.

More specifically, inside the coupling groove 110, a plurality of coupling rails 111 protrude from the inner surface of the coupling groove 110 having a shape and position corresponding to coupling protrusions 222 of the insertion part 220 to be described later. When the insertion part 220 is inserted into the coupling groove 110, the coupling rails 111 are engaged with the coupling protrusions 222 to provide a path along which the coupling protrusions 222 can slide. When the insertion part 220 is completely inserted into the coupling groove 110, engaging protrusions 223 of the cartridge 200 are engaged with and fixed to attachment/detachment buttons 130.

An output switch 120, which is a component that is provided on one side of the housing 100 to manipulate the ultrasound wave output, may be preferably located on the upper surface of the housing 100. When an operator performs an ultrasound treatment on the operator's skin using the handpiece 1, the operator can apply the ultrasound waves to the skin using the output switch 120.

A pair of attachment/detachment buttons 130, which are connected to the inner portion of the coupling groove 110 and allow the operator to manipulate whether or not to separate the cartridge 200, are provided on both sides of the housing 100.

The attachment/detachment buttons 130, which are components for controlling the attachment/detachment for the side surface of the cartridge 200, has recessed spaces therein. When the engaging protrusions 223 to be described later are inserted into the inner spaces of the attachment/detachment buttons 130 and engaged with the attachment/detachment buttons 130, a part of the cartridge 200, that is, the insertion part 220, is inserted into and fixed to the coupling groove 110. When the cartridge 200 needs to be separated, the operator presses the attachment/detachment buttons 130 on both side surfaces to separate the engaging protrusions 223 from the attachment/detachment buttons 130, thereby separating the cartridge 200 from the housing 100.

The power supply part 140 is formed on the inner surface of the coupling groove 110. Specifically, the power supply part 140 is formed at a portion which is brought into contact with the cross section of the insertion part 220. The power supply part 140 provides a power from a medical device main body 2 connected to the housing 100 to the cartridge 200, so that the cartridge 200 can perform non-focused ultrasound treatment.

Cooling water supply holes 150 provide cooling water received from a cooling water storage tank (not shown in the drawing) provided at the medical device main body 2 to a water block 240 in the cartridge 200 so that the heat generated from an ultrasound generation module 211 in the cartridge 200 can be quickly absorbed. The cooling water supply holes 150 have check valves therein to prevent the cooling water from remaining inside the coupling groove 110 even if the cartridge 200 is separated.

The cooling water flowing into the water block 240 circulates inside the water block 240 and absorbs the heat of a cooling block 211b in contact with the water block 240 to return the heat to the medical device main body 2. This will be described in more detail in describing the water block 240 later.

The power supply part 140 and the cooling water supply holes 150 described above are formed on the inner surface of the coupling groove 110 that faces a contact part 210. When the cartridge 200 is coupled, the power supply part 140 and the cooling water supply holes 150 are connected to a substrate 230 and the water block 240, respectively, to provide power and cooling water to the cartridge 200.

The cartridge 200 includes the contact part 210 that is brought into contact with the treatment portion and applies non-focused ultrasound waves to the skin of the subject, the insertion part 220 to be inserted into the coupling groove 110, and the substrate 230 and the water block 240 that allow non-focused ultrasound waves to be outputted in a pre-stored manner.

The contact part 210 is provided on the contact surface of the cartridge 200 that is brought into contact with the treatment portion. The contact part 210 has the ultrasound generation module 211 at one end thereof so that non-focused ultrasound waves generated from the ultrasound generation module 211 is applied to the skin through the contact part 210 and the contact surface.

The ultrasound generation module 211 includes a transducer 211a and the cooling block 211b. The transducer 211a, which substantially generates non-focused ultrasound waves, has a plurality of terminals arranged in a row. The transducer 211a is in close contact with the contact surface but is not in direct contact with the treatment portion.

The cooling block 211b is laminated on the transducer 211a. The heat generated from the transducer 211a is absorbed by the cooling block 211b, thereby preventing excessive heat from being generated in the transducer 211a. Accordingly, it is possible to avoid problems such as burn that may occur during the treatment process by preventing the heat from being transferred to the treatment portion, and to prevent problems from occurring due to the overheating of the transducer 211a.

The water block 240 to be described later is laminated on the cooling block 211b to be in close contact therewith. The heat absorbed by the transducer 211a is transferred to the water block 240 via the cooling block 211*b*, and thus can be discharged to the outside of the cartridge 200.

A stepped portion 212 is formed at the other end of the contact part 210 where the insertion part 220 is formed due to the difference between the cross-sectional area of the contact part 210 and the cross-sectional area of the insertion part 220. When the cartridge 200 is coupled with the housing 100, the stepped portion 212 is caught by the housing 100, so that only the insertion part 220 is inserted into the coupling groove 110 and the other portion is caught by the outer side of the housing 100 and closes the coupling groove 110. Hence, the cartridge 200 is partially inserted into and coupled with the housing 100.

The insertion part 220 protrude from the other end opposite to one end of the cartridge 200 where the contact part 210 is formed. The insertion part 220 protrudes with the same shape as the inner shape of the coupling groove 110 (in a shape corresponding to an inner shape of the coupling groove 110) and is inserted into the coupling groove 110 so that the cartridge 200 is coupled with the housing 100.

In addition, a pressure sensor 221 may be provided on the inner side of the protruding end of the insertion part 220. More preferably, the pressure sensor 221 may be provided inside the contact surface to be in contact with the power supply part 140. Accordingly, the ultrasound generation module 211 can be driven when the cartridge 200 is completely fastened to the housing 100, that is, when the protruding end is completely in contact with the inner surface of the coupling groove 110 and the contact therebetween is detected by the pressure sensor 221. By using the pressure sensor 221, unnecessary operations can be prevented, and the power to the housing 100 can be cut off during the replacement process to prevent safety accidents.

On the outer surface of the insertion part 220, the coupling protrusions 222 protrude vertically from the side surface. The coupling protrusions 222 have a position and shape corresponding to those of the coupling rails 111 described above. Thus, when the operator couples the cartridge 200 with the housing 100, the insertion part 220 inserted into the coupling groove 110 does not simply slide, but the coupling protrusions 222 are mounted on the coupling rails 111 and slide along the extension direction of the coupling rails 111, thereby fixing the cartridge 200 to the correct position.

Further, even if the operator accidentally touches the attachment/detachment buttons 130, the cartridge 200 can be prevented from being immediately separated from the housing 100.

In addition, at the outer side of the insertion part 220, the elastic engaging protrusions 223 protrude from both side surfaces of the insertion part 220 that face the attachment/detachment buttons 130. The engaging protrusions 223 function as the attachment/detachment parts to be engaged by pressing the attachment/detachment buttons 130 on the side surfaces of the insertion part 220 to be inserted into the coupling groove 110.

More specifically, the engaging protrusions 223 have inclination in which the degree of protrusion gradually decreases toward the protruding end. When the insertion part 220 is inserted into the coupling groove 110 along such inclination, the insertion part 220 moves along the inner surface of the coupling groove 110 and is expanded and inserted into the inner sides of the attachment/detachment buttons 130. Accordingly, the insertion part 220 is caught by the inner sides of the attachment/detachment buttons 130, thereby fixing the cartridge 200 to the housing 100. Then, when the attachment/detachment buttons 130 are pressed, the engaging protrusions 223 are separated from the attachment/detachment buttons 130 and inserted into the coupling groove 110, which makes it possible for the operator to separate the cartridge 200 from the housing 100.

The substrate 230 is provided on the inner side of the insertion part 220 and electrically connected to the ultrasound generation module 211. The substrate 230 partially protrudes outward in the protruding direction of the insertion part 220. Hence, when the cartridge 200 is fixed to the housing 100, the substrate 230 and the power supply part 140 are brought into contact with each other and electrically connected, thereby allowing the cartridge 200 to be driven.

The substrate 230 stores commands related to the driving control of the ultrasound generation module 211, so that the ultrasound generation module 211 can be operated using the substrate 230. The substrate 230 is driven and controlled by the output switch 120 so that the non-focused ultrasound waves are generated and applied to the treatment portion according to the intention of the operator.

The water block 240 is in close contact with the cooling block 211*b*, and has therein a flow path through which cooling water can circulate. Nipples 241 that protrude outward from the water block 240 are formed at each end of the flow path.

In other words, it is preferable that the nipples 241 are formed on the upper surface of the water block 240. When the cartridge 200 is fixed to the housing 100, the pair of nipples 241 are inserted into and fitted to the cooling water supply holes 150 so that the inner spaces communicate with each other. Accordingly, the cooling water provided from the cooling water supply holes 150 can be introduced and discharged to absorb the heat generated from the ultrasound generation module 211.

For example, the cooling water supply holes 150 are sealed through the check valves provided therein when they are separated from the nipples 241. When the nipples 241 are inserted into the cooling water supply holes 150, the cooling water supply holes 150 are opened to provide and discharge the cooling water from the handpiece 1.

Figure 4:
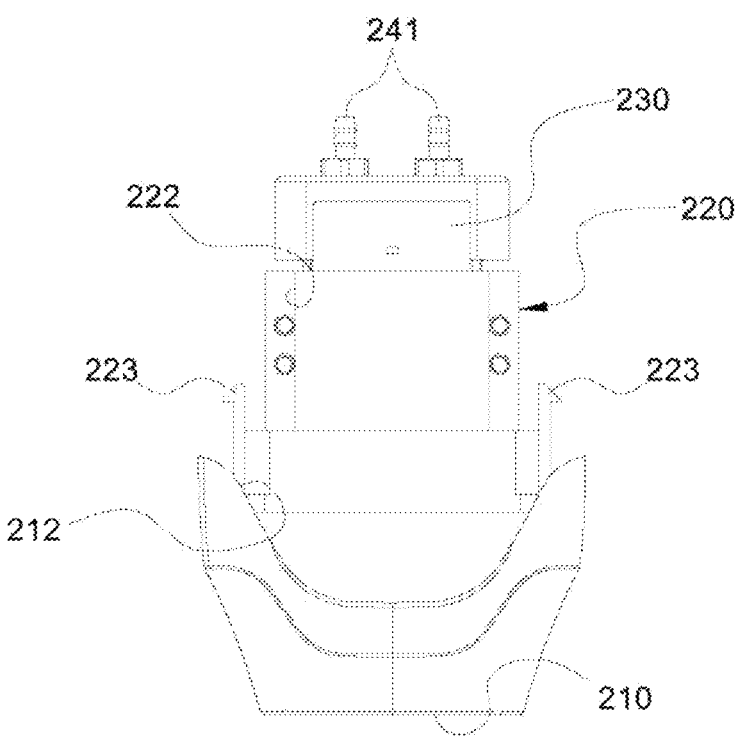
FIG. 4 is a front view showing a cartridge according to the present disclosure.
Figure 5:
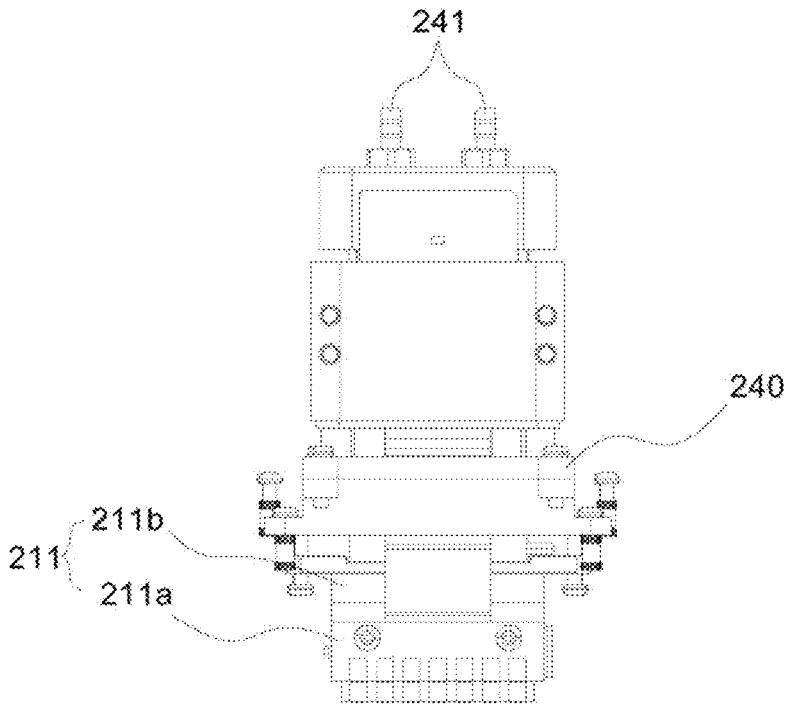
FIG. 5 is a front view showing an ultrasound generation module located inside the cartridge according to the present disclosure.

The nipple 241 has a cylindrical shape as shown in FIG. 4. The nipple 241 has a plurality of protrusions formed along the outer surface thereof at regular intervals and, thus, a plurality of stepped portions are formed, thereby improving airtightness.

With such configuration, the operator can easily replace the cartridge 200 as required. Hence, it is possible to prevent unnecessary handpiece purchases, and also possible to replace the cartridges 200 with various functions according to the intended treatment.

In addition, the housing 100 and the cartridge 200 can be fixed by axial coupling, so that incorrect coupling or unintended separation can be prevented during the process of replacing the cartridge 200. Further, since the cooling water can be continuously supplied to the cartridge 200, it is possible to prevent the heat generated from the ultrasound generation module 211 from being transferred to the treatment portion.

In another embodiment of the present disclosure, the cartridge 200 may further include a skin cooling part for cooling the skin of the subject. The skin cooling part is formed on the contact surface with the skin of the subject, and includes a cooling surface 250 formed along the edge of the contact part 210, and a thermoelectric element (not shown) that continuously cools the cooling surface 250.

Figure 6:
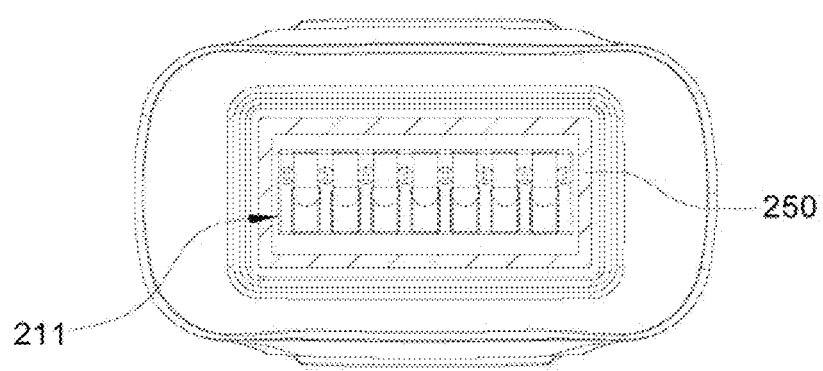
FIG. 6 is a bottom view showing another embodiment of the cartridge according to the present disclosure.

The cooling surface 250 is formed to surround the edge of the contact part 210 as shown in FIG. 6. The cooling surface 250 forms a cooling wall that prevents the heat generated at the treatment portion from being transmitted to other portions by cooling the skin layer from the skin surface (epidermis) to the subcutaneous tissue around the ultrasound waves transmitted from the ultrasound generation module 211 to the skin of the subject simultaneously with the ultrasound treatment, which is advantageous in relieving skin pain and swelling.

The thermoelectric element is provided inside the cartridge 200, but the present disclosure is not limited thereto. When the thermoelectric element is provided inside the housing 100, the thermoelectric element can absorb the heat of the cooling surface 250 and continuously cool the cooling surface 250 using a separate connection member (not shown in the drawing). In this case, the temperature is preferably 0° C. to 5° C., but is not limited thereto.

Figure 7:
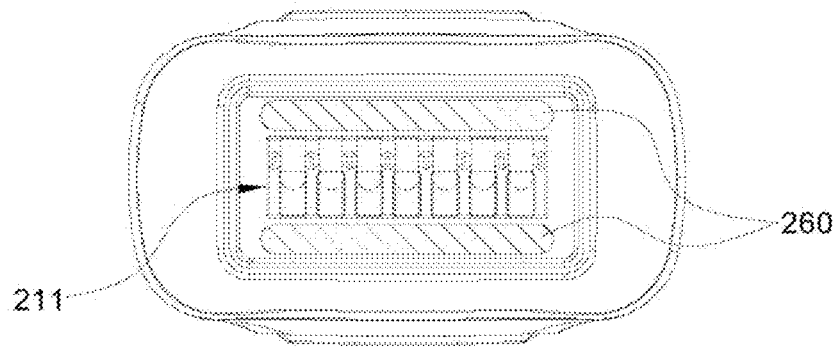
FIG. 7 is a bottom view showing another embodiment of the cartridge according to the present disclosure.
Figure 8:
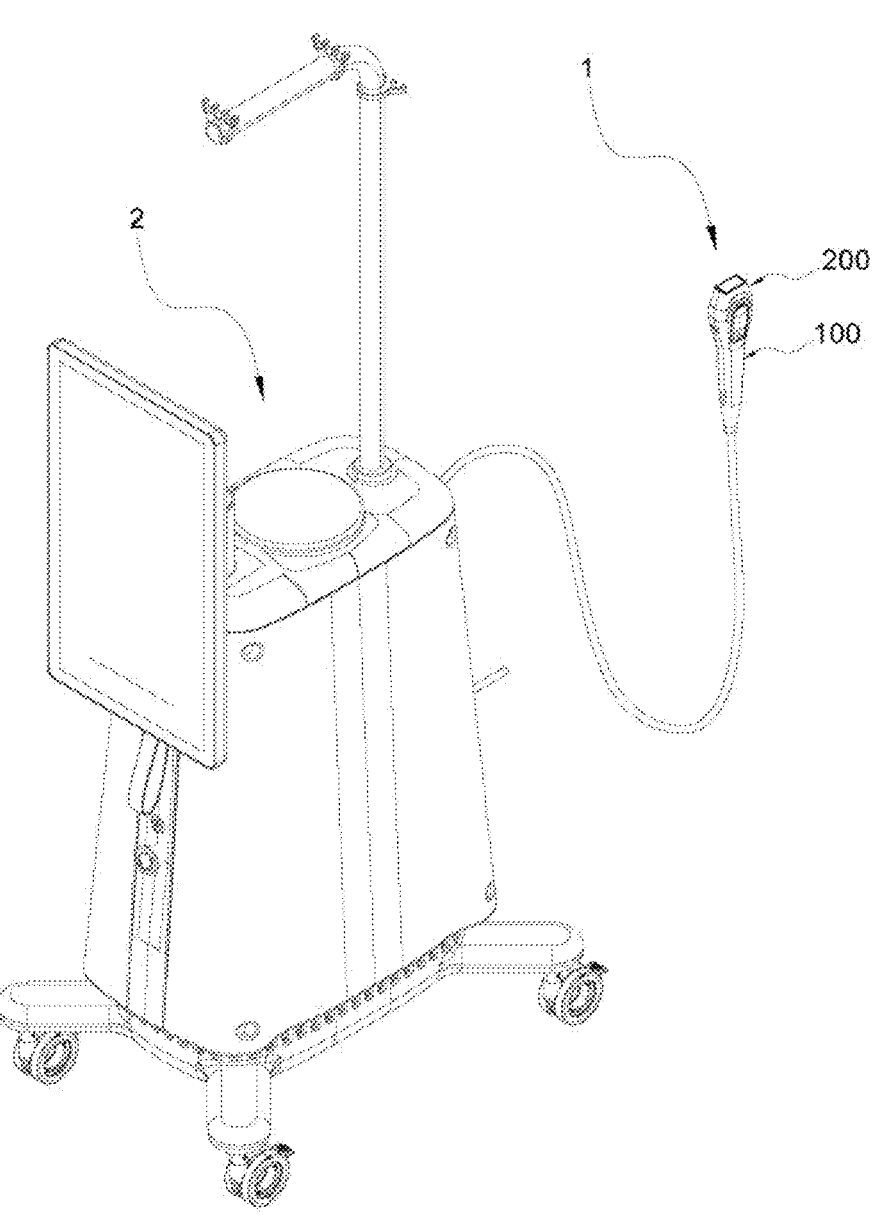
FIG. 8 is a bottom view showing the appearance of a non-focused ultrasound medical device including a cartridge detachable non-focused handpiece according to the present disclosure.

In addition, in another embodiment of the present disclosure, the cartridge 200 may further include a skin stimulation part for electrically stimulating the skin of the subject. The skin stimulation part is formed on the contact surface with the skin of the subject as shown in FIG. 7, and includes an EMS pad 260 and an EMS control module (not shown) that drives and controls the EMS pad 260.

The EMS pad 260 is provided at the contact part 210, and is advantageous in that the skin elasticity is improved by providing an electric muscle stimulation (EMS) function instead of applying non-focused ultrasound waves to the subject's treatment portion.

The EMS control module may be included in the substrate 230, and a separate EMS driving switch (not shown) may be additionally formed on the outer surface of the housing 100 similarly to the output switch 120. Accordingly, the subject can provide the EMS function to the treatment portion using the EMS driving switch.

Although the present disclosure has described the cartridge and handpiece for non-focused ultrasound treatment, the present disclosure is not limited thereto. The handpiece can be replaced with a handpiece for high-intensity focused ultrasound (HIFU) treatment in addition to the non-focused ultrasound treatment, and the ultrasound generation module 211 of the cartridge 200 can be replaced with a micro RF needle, which is an invasive ultrasound electrode, or a non-invasive electrode.

As described above, the optimum embodiments have been shown and described in the drawings and in the specification. Here, specific terms have been used, but the terms are not used to limit the meanings or restrict the technical scope of the present disclosure described in the claims but are just used to describe the present disclosure. Therefore, it will be understood by those of ordinary skilled in the technical field that various modifications and other equivalent embodiments may be made from the above-described embodiments. Hence, the true technical protection scope of the present disclosure should be determined by the technical ideas of the appended claims.

The invention claimed is:

1. A cartridge detachable non-focused handpiece comprising:
    a handpiece-shaped housing; and
    a cartridge that is detachably attached to the housing,
    wherein the housing includes:
        a coupling groove formed on one surface thereof into which a part of the cartridge is inserted and attached;
        an output switch formed on an upper surface thereof and configured to manipulate an ultrasound wave output;

attachment/detachment buttons formed on both side surfaces thereof and configured to control attachment and detachment of side surface of the cartridge; and
    a power supply part configured to supply a power to the cartridge, wherein the cartridge includes:
    a contact part formed at one end thereof, the contact part having an ultrasound generation module embedded therein and being configured to contact a skin of a subject;
    an insertion part formed at the other end thereof, the insertion part being protruded in a shape corresponding to an inner shape of the coupling groove and having an attachment/detachment part which is formed at side surfaces of the insertion part to be inserted into the coupling groove and is engageable by pressing the detachment buttons; and
    a substrate electrically connected to the power supply part to drive the ultrasound generation module,
    wherein in the cartridge, the insertion part is inserted into and fixedly attached to the coupling groove, and the ultrasound generation module is configured to generate non-focused ultrasound waves using the power supply part,
    wherein the ultrasound generation module includes:
    a transducer configured to generate ultrasound waves; and
    a cooling block configured to absorb heat from the transducer,
    a water block to be in contact with an upper surface of the cooling block and through which cooling water moves, and a pair of nipples formed on an upper surface of the water block and through which cooling water is introduced and discharged are formed at the cartridge,
    cooling water supply holes into which the nipples are inserted to provide cooling water to the water block are formed at the housing, and
    when the cartridge is coupled with the housing, the cooling water provided from the cooling water supply holes circulates through the water block and absorbs heat from the transducer, and
    wherein the cooling water supply holes have therein check valves so that the nipples are sealed when the nipples are separated from the cooling water supply holes, and the cooling water supply holes are opened when the nipples are inserted into the cooling water supply holes to provide and discharge the cooling water from the handpiece.

2. The cartridge detachable non-focused handpiece of claim 1, wherein the insertion part has a pressure sensor embedded in a contact surface to be in contact with the power supply part, and
    the pressure sensor is configured to detect whether or not the cartridge and the housing are coupled, and the ultrasound generation module is configured to be driven only when the coupling of the cartridge and the housing is detected.

3. The cartridge detachable non-focused handpiece of claim 1, wherein a coupling protrusion protrudes from an outer surface of the insertion part,
    a coupling rail to be engaged with the coupling protrusion is formed on an inner surface of the coupling groove, and
    the coupling protrusion slides along the coupling rail when the insertion part is inserted into the coupling groove.

4. The cartridge detachable non-focused handpiece of claim 1, wherein the cartridge further includes:

a skin cooling part configured to cool the skin of the subject, wherein the skin cooling part includes:

a cooling surface formed along an edge of the contact part to cool the skin of the subject; and a thermoelectric element configured to absorb heat from the cooling surface;

wherein the cooling surface forms a cooling wall configured to cool the skin layer of the subject around the ultrasound waves transmitted from the ultrasound generation module to the skin of the subject.

5. The cartridge detachable non-focused handpiece of claim 1, wherein the cartridge further includes:

a skin stimulation part configured to stimulate the skin of the subject, wherein the skin stimulation part includes:

an EMS pad that is provided at the contact part and provide electrical stimulation to a treatment portion of the subject; and an EMS control module configured to drive and control the EMS pad, and wherein an EMS driving switch configured to control driving of the EMS control module is formed on an outer surface of the housing.

6. A non-focused ultrasound medical device including the cartridge detachable non-focused handpiece described in claim 1.

* * * * *